United States Patent
Veronesi et al.

(10) Patent No.: US 10,499,879 B2
(45) Date of Patent: Dec. 10, 2019

(54) SYSTEMS AND METHODS FOR DISPLAYING INTERSECTIONS ON ULTRASOUND IMAGES

(71) Applicant: General Electric Company, Schenectady, NY (US)

(72) Inventors: Federico Veronesi, Bologna (IT); Olivier Gerard, Oslo (NO); Stein Rabben, Tarnasen (NO)

(73) Assignee: General Electric Company, Schenectady, NY (US)

( * ) Notice: Subject to any disclaimer, the term of this patent is extended or adjusted under 35 U.S.C. 154(b) by 281 days.

(21) Appl. No.: 15/610,410

(22) Filed: May 31, 2017

(65) Prior Publication Data

US 2018/0344290 A1 Dec. 6, 2018

(51) Int. Cl.
| | | |
|---|---|---|
| *G06K 9/00* | (2006.01) | |
| *A61B 8/00* | (2006.01) | |
| *G06T 7/00* | (2017.01) | |
| *G06T 19/00* | (2011.01) | |
| *A61B 8/08* | (2006.01) | |
| *G06T 15/08* | (2011.01) | |

(52) U.S. Cl.
CPC ........... *A61B 8/466* (2013.01); *A61B 8/00* (2013.01); *A61B 8/483* (2013.01); *G06T 7/00* (2013.01); *G06T 15/08* (2013.01); *G06T 19/00* (2013.01); *G06T 2210/21* (2013.01); *G06T 2210/41* (2013.01); *G06T 2219/008* (2013.01); *G06T 2219/028* (2013.01)

(58) Field of Classification Search
None
See application file for complete search history.

(56) References Cited

U.S. PATENT DOCUMENTS

| | | | | |
|---|---|---|---|---|
| 2010/0265251 A1* | 10/2010 | Vining | .................... | G06T 7/11 345/420 |
| 2012/0245465 A1* | 9/2012 | Hansegard | ............ | A61B 8/466 600/443 |
| 2017/0084029 A1* | 3/2017 | Piazza | .................. | A61B 5/1075 |

FOREIGN PATENT DOCUMENTS

| | | |
|---|---|---|
| EP | 1 929 956 A2 | 6/2008 |
| GB | 2 431 308 A | 4/2007 |
| WO | 2004/095378 A1 | 11/2004 |
| WO | 2011/009121 A1 | 1/2011 |

OTHER PUBLICATIONS

International Search Report and Written Opinion issued in connection with corresponding PCT Application No. PCT/US2018/034232 dated Aug. 17, 2018.

* cited by examiner

*Primary Examiner* — Atiba O Fitzpatrick
(74) *Attorney, Agent, or Firm* — McCoy Russell LLP (57) ABSTRACT

Methods and systems are provided for visualizing intersection information on ultrasound images. In one embodiment, a method comprises rendering a three-dimensional (3D) image and at least one two-dimensional (2D) image from a 3D dataset, generating a 3D model of at least a subset of the 3D dataset, identifying intersections between the 3D image, the at least one 2D image, and the 3D model, and displaying the 3D model and the intersections on the 3D model. In this way, a user may easily visualize how the 2D slice planes are positioned with respect to the volume rendering.

20 Claims, 4 Drawing Sheets

SYSTEMS AND METHODS FOR DISPLAYING INTERSECTIONS ON ULTRASOUND IMAGES

FIELD

Embodiments of the subject matter disclosed herein relate to ultrasound imaging, and more particularly, to visualizing intersection information on ultrasound images.

BACKGROUND

When displaying two-dimensional (2D) renderings of three-dimensional (3D) volume data, such as in a 3D ultrasound dataset, it may be desirable to visualize one or more surfaces together with the volume data in a manner to allow a visual determination of where the surfaces intersect the volume. For example, it may be desirable to visualize intersections between volume data and planes. In 3D cardiac ultrasound, where it is common to display one or more 2D slice planes reconstructed from a 3D ultrasound data volume, it is important to be able to determine from the displayed information how the 2D slice planes are positioned with respect to the volume rendering to identify the relationship between the two visualization techniques.

However, navigating the 3D ultrasound data volume may be difficult for users. Consequently, a user may encounter difficulties when adjusting the 2D views or discerning the relationship between the 2D slices and the 3D image volume. Further still, the 3D image volume is typically colorized, and so the user may also encounter difficulties when ascertaining the position of the 2D slices within the 3D image volume, even with the visualization of the intersections.

BRIEF DESCRIPTION

In one embodiment, a method comprises rendering a three-dimensional (3D) image and at least one two-dimensional (2D) image from a 3D dataset, generating a 3D model of at least a subset of the 3D dataset, identifying intersections between the 3D image, the at least one 2D image, and the 3D model, and displaying the 3D model and the intersections on the 3D model. In this way, a user may easily visualize how the 2D slice planes are positioned with respect to the volume rendering.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of ultrasound imaging. In particular, systems and methods are provided for visualizing intersection information on ultrasound images with the aid of a three-dimensional model. A three-dimensional ultrasound dataset may be acquired using an ultrasound system, such as the ultrasound system depicted in FIG. 1. A method, such as the method depicted in FIG. 2, for visualizing intersections between 2D image slices and the 3D ultrasound dataset may include generating a 3D model of a region of interest (ROI) to aid with visualizing the intersections. For example, a graphical user interface, such as the graphical user interfaces depicted in FIGS. 3 and 4, may include a visualization of the 3D model with intersection information displayed thereon, thereby enabling a user to easily navigate the 3D dataset and select planes within the 3D dataset for rendering.

It should be appreciated that while the various embodiments are described herein with respect to ultrasound imaging, the methods described herein may be implemented with other 3D imaging modalities, including but not limited to computed tomography (CT), magnetic resonance imaging (MRI), positron emission tomography (PET), single photon emission computed tomography (SPECT), and so on. For example, 3D models of an ROI may be utilized to navigate 3D CT datasets and select 2D slices to be displayed.

Figure 1:
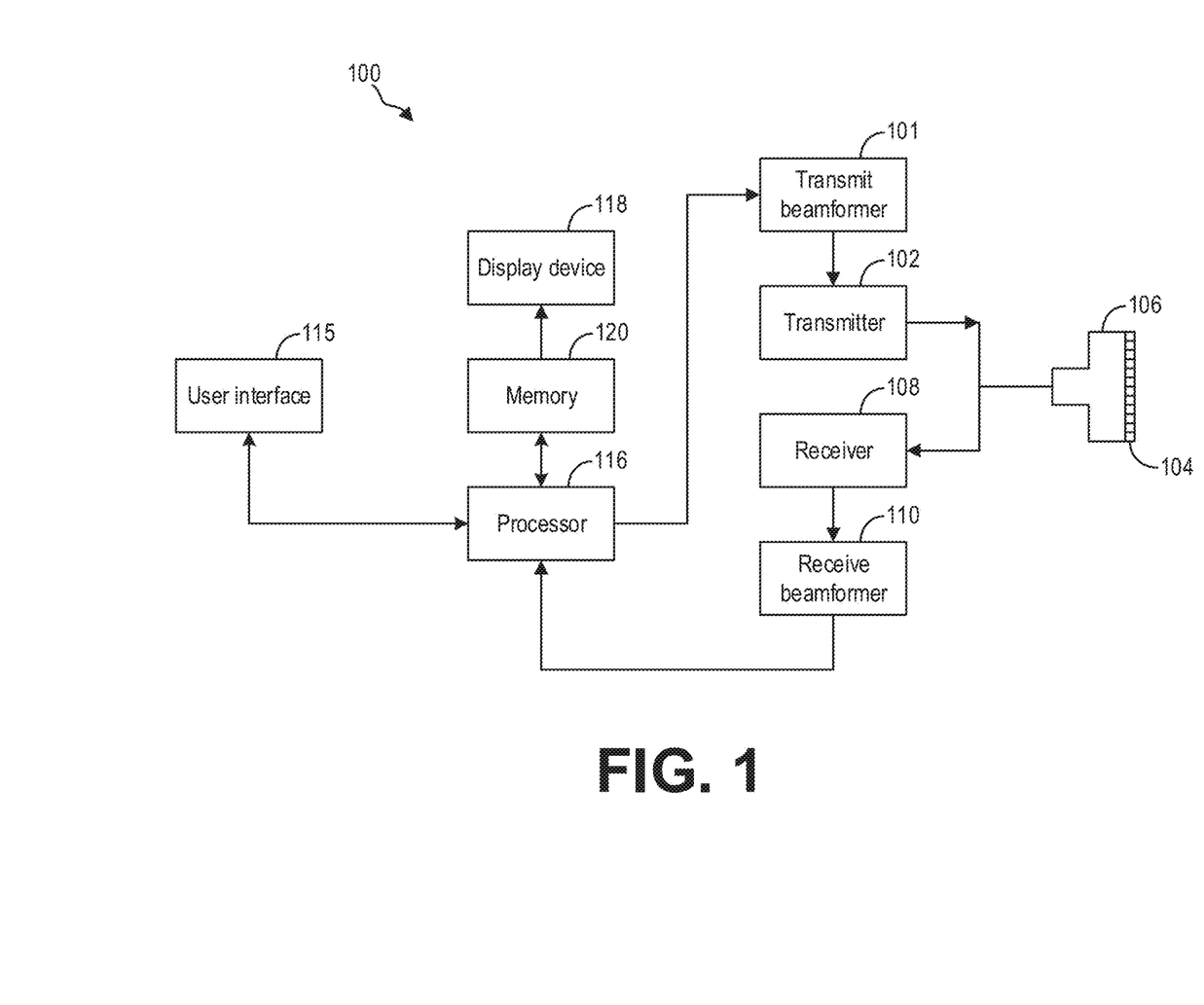
FIG. 1 shows an example ultrasonic imaging system.

FIG. 1 is a schematic diagram of an ultrasound imaging system 100 in accordance with an embodiment of the invention. The ultrasound imaging system 100 includes a transmit beamformer 101 and a transmitter 102 that drive transducer elements 104 within a probe 106 to emit pulsed ultrasonic signals into a body (not shown). A variety of geometries of probes and transducer elements may be used. The pulsed ultrasonic signals are back-scattered from structures in the body, such as blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound system.

A user interface 115 may be used to control operation of the ultrasound imaging system 100, including controlling the input of patient data, changing a scanning or display parameter, and the like. The user interface 115 may include a graphical user interface configured for display on a display device 118. The graphical user interface may include information to be output to a user (such as ultrasound images, patient data, etc.) and may also include menus or other elements through which a user may enter input to the computing system. In examples described in more detail below with respect to FIGS. 2-4, the user interface may receive inputs from a user indicating, for example, adjustments to the position of planes to be imaged. The user interface 115 may include one or more of the following: a rotary, a mouse, a keyboard, a trackball, a touch-sensitive display, hard keys linked to specific actions, soft keys that may be configured to control different functions, and a graphical user interface.

The ultrasound imaging system 100 also includes a processor 116 to control the transmit beamformer 101, the transmitter 102, the receiver 108, and the receive beamformer 110. The processor 116 is in electronic communication with the probe 106. For the purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the display may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in the memory 120, from which the images are read and displayed.

Figure 2:
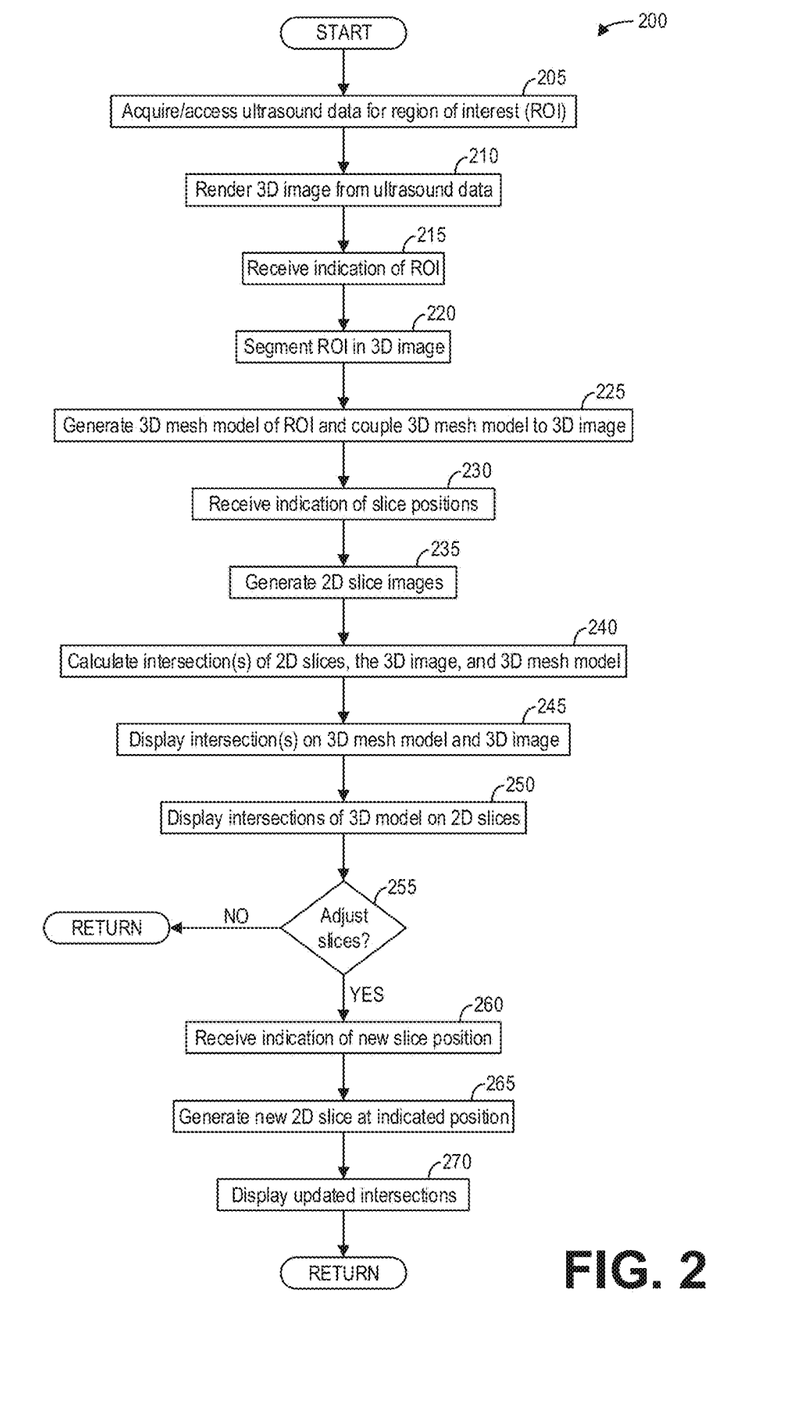
FIG. 2 shows a high-level flow chart illustrating an example method for displaying intersection information on an ultrasound image according to an embodiment.

FIG. 2 shows a high-level flow chart illustrating an example method 200 for displaying intersection information on an ultrasound image according to an embodiment. Method 200 will be described herein with reference to the system and components depicted in FIG. 1, though it should be understood that the method may be applied to other systems and components without departing from the scope of the present disclosure. Method 200 may be carried out by processor 116, and may be stored as executable instructions in non-transitory memory of the processor 116.

Method 200 begins at 205. At 205, method 200 includes acquiring ultrasound data for a region of interest (ROI). In some examples, the ROI may comprise a structure or object, for example an organ such as a human heart or a region thereof. The ultrasound data may comprise a 3D ultrasound dataset or in some examples a 4D ultrasound dataset. For example, the ultrasound data may comprise a volume of data including 3D color Doppler data over time, such as over one or more heart cycles (e.g., ultrasound echocardiography data), and may be stored in a memory device.

In some examples, ultrasound data that has been previously acquired and stored in the memory device may be accessed for processing. In such examples, acquiring ultrasound data for the ROI may comprise accessing a previously-acquired 3D ultrasound dataset in memory, such as the memory 120.

At 210, method 200 includes rendering a 3D image volume from the ultrasound data. For example, a 3D image volume or 3D image may be reconstructed from the 3D ultrasound dataset using any suitable 3D volumetric image reconstruction technique. In some embodiments, the 3D volume dataset is displayed in real-time, for example, on the display device 118.

At 215, method 200 includes receiving an indication of the ROI. The indication of the ROI may comprise an indication received, from a user via a user interface such as user interface 115, of a particular region or organ of interest. In some examples, the indication may include two or more ROIs. For example, the user may desire to image the heart and more specifically the mitral valve of the heart, and therefore may indicate that the ROI includes both the heart and the mitral valve.

It should be appreciated that in some examples, the method may receive an indication of the ROI prior to acquiring the ultrasound dataset. For example, 215 may be carried out prior to 205, such that the acquisition of the ultrasound is based on the received indication of the ROI.

Continuing at 220, method 200 includes segmenting the ROI in the 3D image. The ROI may be segmented in the 3D image volume using known segmentation techniques, such as threshold segmentation or another suitable segmentation algorithm.

At 225, method 200 includes generating a 3D mesh model of the ROI. The 3D mesh model of the ROI may be retrieved from a digital repository of 3D mesh models corresponding to different organs or anatomies, as an illustrative and non-limiting example. As another example, the method may generate a 3D mesh model of the segmented ROI obtained at 220. In yet another example, the method may retrieve a generic 3D mesh model of the ROI from a digital repository and fit the mesh model to the segmented ROI obtained at 220.

Method 200 further includes coupling the 3D mesh model to the 3D image. For example, one or more points of the 3D mesh model may be linked to one or more corresponding voxels of the ROI in the 3D image. In this way, the scale and orientation of the 3D mesh model may correspond to the scale and orientation of the ROI in the 3D image. The coupling may be carried out automatically or in some examples may be carried out with assistance from user input. For example, the method may automatically identify corresponding points in the 3D mesh model and the 3D image, or a user may manually identify, via the user interface 115 for example, the corresponding points in the 3D mesh model and the 3D image.

Continuing at 230, method 200 includes receiving an indication of one or more slice positions. For example, one or more planes or slices in the 3D mesh model may be selected or indicated by a user, for example via the user interface 115. For example, the user may manually move or position virtual slices on the screen to selected different views to display. Thus, based on one or more user-selected or—marked planes, which may be selected image views, a determination is made as to the coordinates of the plane(s) through the 3D volume dataset corresponding to the location in the 3D mesh model. In some examples, the voxels within the 3D volume dataset corresponding to the user-selected plane(s) are determined.

As another example, one or more planes may be automatically identified and indicated based on the indication of the ROI. For example, standard views may be predetermined for a given ROI, and the indication of the slice positions corresponding to the standard views may be automatically retrieved and/or generated based on the indication of the ROI as well as the 3D mesh model. In other words, the slice positions or planes may be located at fixed pre-determined positions relative to the data volume or the ultrasound probe. For example, two orthogonal slice planes corresponding to the azimuth and elevation planes of the acquired ultrasound ROI may be positioned such that the planes intersect the center of the data volume. As another example, three slice planes may be rotated about a common axis (such as the probe axis) where the planes are by default oriented to provide visualization of a four chamber view, a two chamber view, and a long axis view of the left ventricle of the heart. The user may or may not modify the position and orientation of these planes.

At 235, method 200 includes generating one or more 2D slice image(s) from the 3D ultrasound dataset based on the indication of the one or more slice positions. The one or more 2D slice images may be displayed on a display device, such as display device 118, alongside the 3D mesh model and the 3D image volume.

At 240, method 200 includes calculating intersection(s) of the 2D slice(s), the 3D image volume, and the 3D mesh model, which may be easily carried out due to the coupling of the 3D mesh model to the 3D image volume. Calculating the intersections of the 2D slices and the 3D mesh model comprises calculating the location of the planes in the 3D mesh model that correspond to the 2D slices, as well as calculating the location in the 2D slices that intersect with the 3D mesh model.

At 245, method 200 includes displaying the intersection(s) on the 3D mesh model and the 3D image. For example, lines or curves corresponding to the position of the 2D slices in the 3D mesh model may be displayed or visually overlaid on the 3D mesh model to indicate the intersections of the 2D slices with the 3D mesh model. Similarly, the intersections of the 2D slices with the 3D mesh model may also be displayed or visually overlaid on the 3D image. Alternatively, pixels or voxels of the 3D image corresponding to the intersection of the 2D slices with the 3D image may be colorized or otherwise adjusted to visually indicate the intersections in the 3D image.

The intersections may be colorized to distinguish the intersections from each other, as well as to provide a visual indication of which 2D slice the intersection corresponds to. For example, one or more visual indicators may be displayed or visually overlaid on the 2D slice; the one or more visual indicators may be colorized similar to the corresponding intersection curve displayed on the 3D mesh model to provide a visual correspondence between the intersection curve and the 2D slice. It should be appreciated that in addition to or as an alternative to colorizing the intersection curves, any parameter may be adjusted to identify or highlight the intersection along the surface. For example, the color, transparency, intensity, and/or value of the pixels corresponding to the identified intersection voxels may be changed.

At 250, method 200 includes displaying intersection(s) of the 3D model with the 2D slices on the 2D slices. For example, one or more intersection curves may be displayed or visually overlaid on the 2D slices to indicate the intersection of the 2D slice with the 3D mesh model. Alternatively, pixels of the 2D slice corresponding to the location of the intersection(s) may be colorized or otherwise adjusted to indicate the location of the intersection on the 2D slice.

At 255, method 200 includes determining if one or more of the 2D slice(s) will be adjusted. Determining if one or more of the 2D slices will be adjusted comprises determining if user input regarding a new position for a 2D slice on the 3D mesh model and/or the 3D image volume. For example, the user may select an intersection displayed on the 3D mesh model and manually move or adjust the position of the intersection within the 3D mesh model, for example via the user interface 115. In some examples, the user may adjust the display of the 3D mesh model, for example by scaling the display of the 3D mesh model and/or rotating or otherwise changing the displayed perspective of the 3D mesh model. Changing the display of the 3D mesh model makes it easier for the user to navigate the 3D volume to select a new position for a 2D slice.

If there is no user input relating to a new position for a 2D slice, then there are no slice adjustments ("NO"), and method 200 returns. However, if there is user input relating to a new position for a 2D slice, there is a slice adjustment ("YES"), and method 200 continues to 260. At 260, method 200 includes receiving an indication of a new slice position, for example via the user interface 115.

At 265, method 200 includes generating and displaying a new 2D slice from the ultrasound dataset at the indicated position. At 270, method 200 includes displaying the updated intersections between the new 2D slice, the 3D mesh model, and the 3D image. Method 200 then returns.

It should be appreciated that although the method 200 is described with regard to 3D ultrasound datasets, method 200 may be applied to four-dimensional datasets comprising three spatial dimensions plus time. Furthermore, it should be appreciated that while method 200 is described hereinabove with respect to ultrasound imaging, method 200 may be implemented with other 3D imaging modalities, including but not limited to computed tomography (CT), magnetic resonance imaging (MRI), positron emission tomography (PET), single photon emission computed tomography (SPECT), and so on. For example, the 3D dataset may comprise a CT dataset or an MRI dataset.

Figure 3:
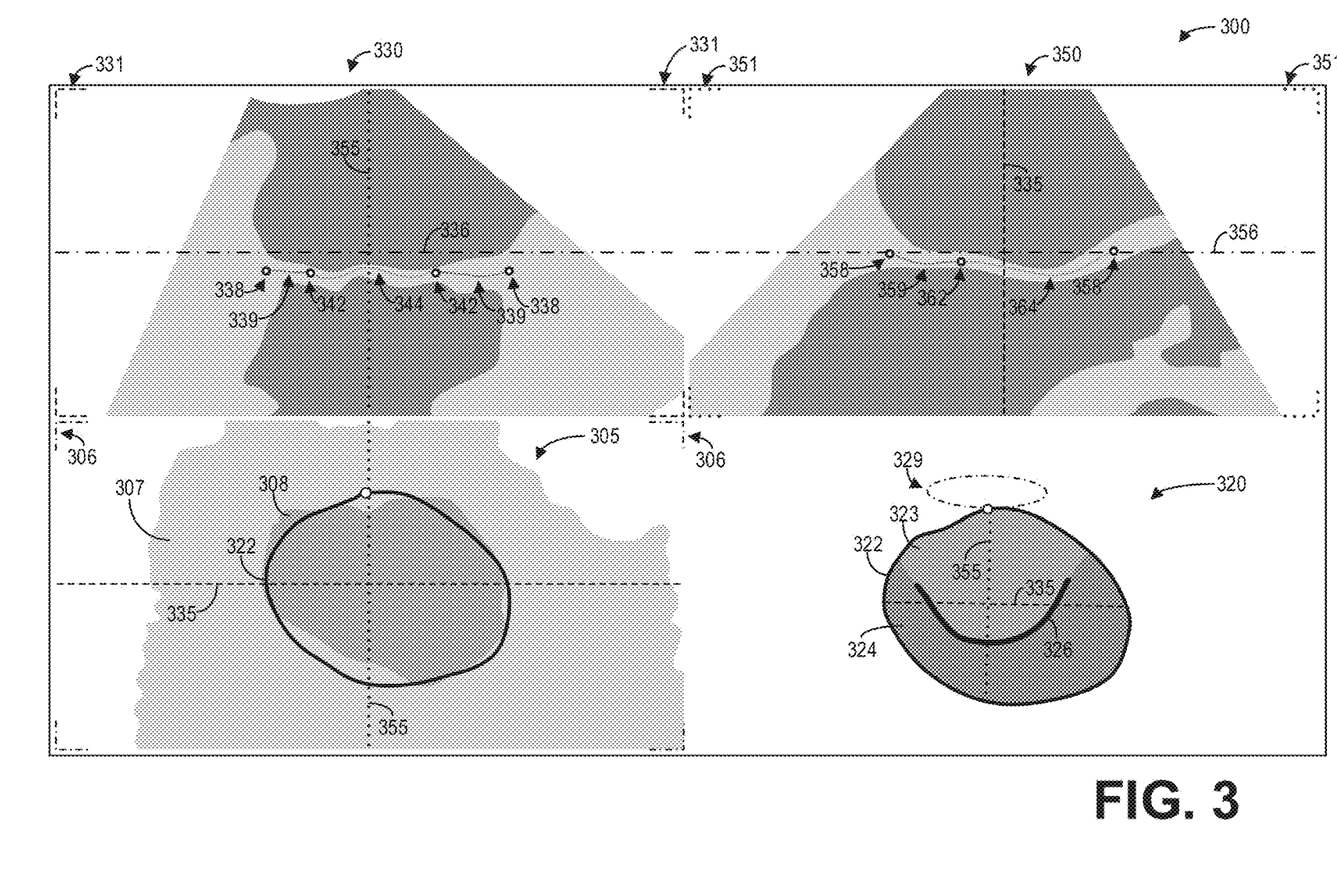
FIG. 3 shows an example graphical user interface for displaying intersection information on an ultrasound image for two two-dimensional slices.
Figure 4:
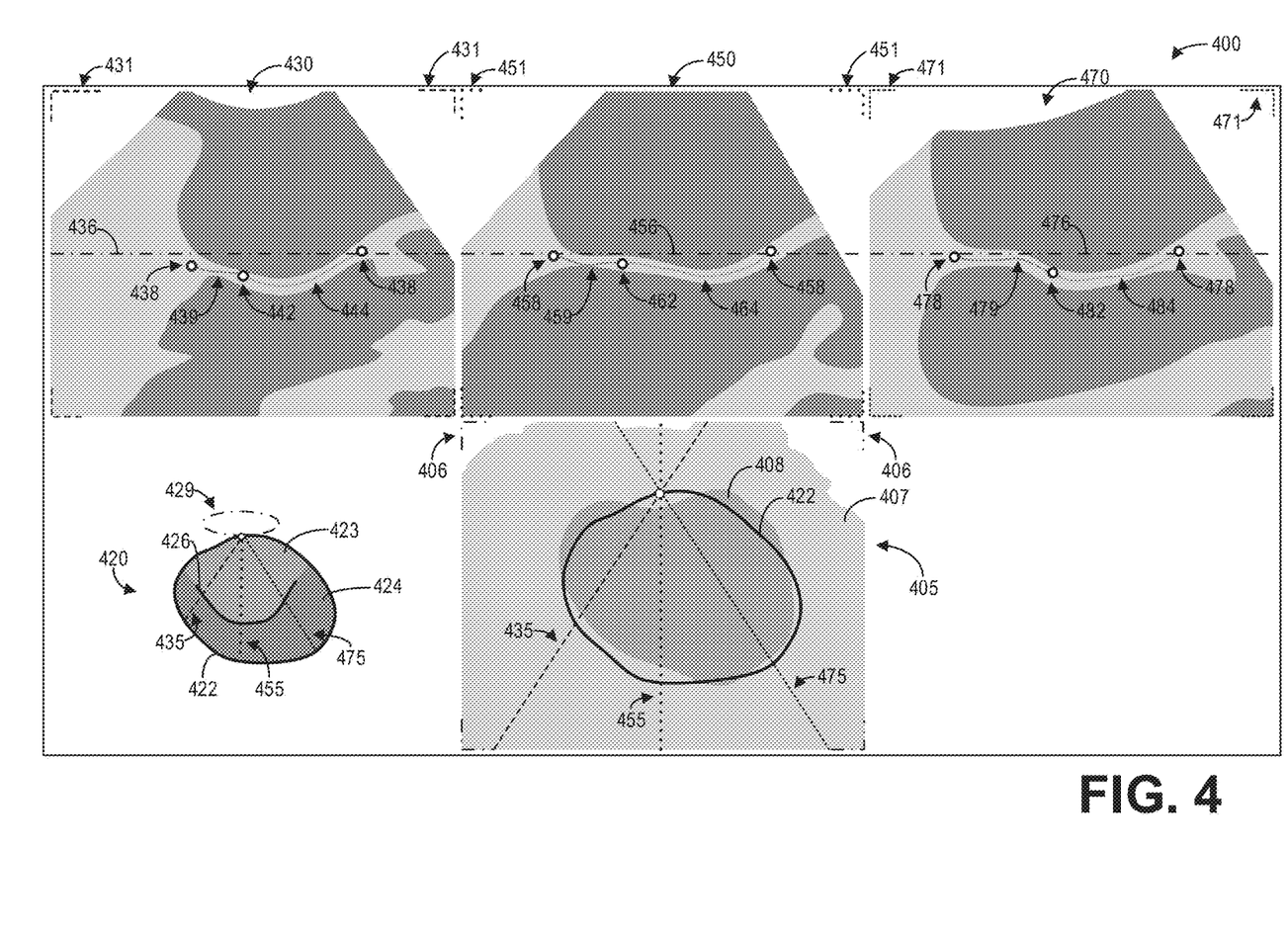
FIG. 4 shows an example graphical user interface for displaying intersection information on an ultrasound image for three two-dimensional slices.

FIGS. 3 and 4 illustrate example implementations of the method depicted in FIG. 2. Specifically, FIG. 3 shows an example graphical user interface 300 for displaying intersection information on an ultrasound image for two 2D slices. Graphical user interface 300 may be displayed, for example, on a display device such as display device 118.

Graphical user interface 300 may include a 3D image volume 305 including an ROI 308, a 3D mesh model 320 of the ROI 308, a first 2D slice 330, and a second 2D slice 350. The 3D image volume 305 may comprise a rendering of the 3D ultrasound dataset, and may be generated at 210 as discussed hereinabove with regard to FIG. 2. As depicted, a region 307 of tissue and other anatomical structures surrounds the ROI 308. It should be appreciated that the depiction of both the region 307 and the ROI 308 in the 3D image volume 305 are simplified for the purposes of this disclosure.

As depicted, the 3D mesh model 320 of the ROI 308 may be displayed adjacent to the 3D image volume 305 in the graphical user interface 300. The 3D mesh model 320 includes a boundary 322 of the ROI, a first region 323, a second region 324, and a structure 326. The first region 323 and the second region 324 may correspond, as non-limiting examples, to different regions of the ROI. The structure 326 may correspond to an anatomical structure within the ROI. For example, the structure 326 may correspond to a mitral valve. The boundary 322 of the 3D mesh model 320 may be visually overlaid on the 3D image volume 305. In some examples, a user may adjust the boundary 322 to match the boundary of the ROI 308.

The first 2D slice 330 and the second 2D slice 350 may comprise different 2D views of the 3D ultrasound dataset. The intersections between the 2D slices 330 and 350 with the 3D image volume 305 may be visually depicted in the 3D mesh model 320. For example, the plane corresponding to the first 2D slice 330 may be represented as a line or intersection 335 on the 3D mesh model 320, while the plane corresponding to the second 2D slice 350 may be represented as a line or intersection 355 on the 3D mesh model 320. The intersections 335 and 355 may also be displayed or overlaid on the 3D image volume 305.

Further, the intersections 335 and 355 may be colorized or rendered with certain patterns (e.g., dash and dot configurations as depicted in FIG. 3) to distinguish the intersections from each other. In addition, the graphical user interface 300 may include a plurality of visual indicators such as indicators 331, 351, and 306 associated with the 2D slices 330 and 350 as well as the 3D image volume 305. The visual indicators may be colorized or rendered with particular patterns to provide a visual connection between the images and the intersections. For example, the intersection 335 may be rendered with a first color or a first pattern (as depicted, a dashed line), and the visual indicators 331 may be similarly rendered with the first color or the first pattern to indicate that the intersection 335 corresponds to the intersection of the first 2D slice 330 with the 3D image volume 305. Similarly, the intersection 355 may be rendered with a second color or a second pattern (as depicted, a dotted line), and the visual indicators 351 may be similarly rendered with the second color or the second pattern to indicate that the intersection 355 corresponds to the intersection of the second 2D slice 350 with the 3D image volume 305.

In some examples, the display of the 3D mesh model 320 may include a visual indicator 329 which indicates the orientation of the 3D mesh model 320 with respect to the display of the 3D image volume 305. The visual indicator 329 may be colorized or otherwise visually styled to correspond to the visual indicators 306 that may outline or otherwise delineate the display of the 3D image volume 305 in the graphical user interface 300. Further, the orientation 329 of the 3D image volume with respect to the 3D mesh model 320 may be displayed on the 2D slices 330 and 350 as intersection lines 336 and 356, respectively.

In some examples, the intersection of the 2D slices 330 and 350 with the 3D mesh model 320 may be displayed on the 2D slices. For example, the intersection of the boundary 322 with respect to the 2D image slice 330 may be displayed on the 2D image slice as intersections 338. The intersections of the 2D image slice 330 with the structure 326 may be displayed on the 2D image slice 330 as intersections 342. Further, the intersections of the 2D image slice 330 with the first region 323 of the 3D mesh model 320 may be displayed on the 2D image slice 330 as intersection 344, while the intersections of the 2D image slice 330 with the second region 324 of the 3D mesh model 320 may be displayed on the 2D image slice 330 as intersections 339. The intersections displayed on the 2D image slice 330 may be colorized or otherwise styled to visually correspond to the regions and boundaries of the 3D mesh model 320, as depicted. Similarly, the intersections of the second 2D image slice 350 with the 3D mesh model 320 may be displayed on the 2D image slice 350 as intersections 358, 359, 362, 364, and 358. In this way, the user may easily identify the position of anatomical structures and regions of interest within the 2D image slices.

As discussed hereinabove with regard to FIG. 2, a user may rotate or scale the 3D mesh model 320 to obtain a different perspective or view of the ROI. The user may also select one or more of the intersections 335 and 355, and adjust the position of the intersections 335 and 355. Accordingly, the corresponding 2D image slice will be updated with a new 2D image slice rendered from ultrasound data at the adjusted intersection positions. Further, the intersection information may be updated on each image.

As another illustrative example, FIG. 4 shows an example graphical user interface 400 for displaying intersection information on an ultrasound image for three 2D slices. Graphical user interface 400 may be displayed, for example, on a display device such as display device 118.

Graphical user interface 400 may include a 3D image volume 405 including an ROI 408, a 3D mesh model 420 of the ROI 408, a first 2D slice 430, a second 2D slice 450, and a third 2D slice 470. The 3D image volume 405 may comprise a rendering of the 3D ultrasound dataset, and may be generated at 210 as discussed hereinabove with regard to FIG. 2. As depicted, a region 407 of tissue and other anatomical structures surrounds the ROI 408. It should be appreciated that the depiction of both the region 407 and the ROI 408 in the 3D image volume 405 are simplified for the purposes of this disclosure.

As depicted, the 3D mesh model 420 of the ROI 408 may be displayed adjacent to the 3D image volume 405 in the graphical user interface 400. The 3D mesh model 420 includes a boundary 422 of the ROI, a first region 423, a second region 424, and a structure 426. The first region 423 and the second region 424 may correspond, as non-limiting examples, to different regions of the ROI. The structure 426 may correspond to an anatomical structure within the ROI. For example, the structure 426 may correspond to a mitral valve. The boundary 422 of the 3D mesh model 420 may be visually overlaid on the 3D image volume 405. In some examples, a user may adjust the boundary 422 to match the boundary of the ROI 408.

The first 2D slice 430, the second 2D slice 450, and the third 2D slice 470 may comprise different 2D views of the 3D ultrasound dataset. The intersections between the 2D slices 430, 450, and 470 with the 3D image volume 405 may be visually depicted in the 3D mesh model 420. For example, the plane corresponding to the first 2D slice 430 may be represented as a line or intersection 435 on the 3D mesh model 420, the plane corresponding to the second 2D slice 450 may be represented as a line or intersection 455 on the 3D mesh model 420, and the plane corresponding to the third 2D slice 470 may be represented as a line or intersection 475 on the 3D mesh model 420. The intersections 435, 455, and 475 may also be displayed or overlaid on the 3D image volume 405 to indicate the positional relationship between the images and image volumes.

Further, the intersections 435, 455, and 475 may be colorized or rendered with certain patterns (e.g., dash and dot configurations as depicted in FIG. 4) to distinguish the intersections from each other. In addition, the graphical user interface 400 may include a plurality of visual indicators such as indicators 431, 451, 471, and 406 associated with the 2D slices 430, 450, and 470 as well as the 3D image volume 405. The visual indicators may be colorized or rendered with particular patterns to provide a visual connection between the images and the intersections. For example, the intersection 435 may be rendered with a first color or a first pattern (as depicted, a dashed line), and the visual indicators 431 may be similarly rendered with the first color or the first pattern to indicate that the intersection 435 corresponds to the intersection of the first 2D slice 430 with the 3D image volume 405. Similarly, the intersection 455 may be rendered with a second color or a second pattern (as depicted, a dotted line), and the visual indicators 451 may be similarly rendered with the second color or the second pattern to indicate that the intersection 455 corresponds to the intersection of the second 2D slice 450 with the 3D image volume 405. Further, the intersection 475 may be rendered with a third color or a third pattern (as depicted, a half-dash line), and the visual indicators 471 may be similarly rendered with the second color or the second pattern to indicate that the intersection 475 corresponds to the intersection of the third 2D slice 470 with the 3D image volume 405.

In some examples, the display of the 3D mesh model 420 may include a visual indicator 429 which indicates the orientation of the 3D mesh model 420 with respect to the display of the 3D image volume 405. The visual indicator 429 may be colorized or otherwise visually styled to correspond to the visual indicators 406 that may outline or otherwise delineate the display of the 3D image volume 405 in the graphical user interface 400. Further, the orientation 429 of the 3D image volume with respect to the 3D mesh model 420 may be displayed on the 2D slices 430, 450, and 470 as intersection lines 436, 456, and 476, respectively.

In some examples, the intersection of the 2D slices 430, 450, and 470 with the 3D mesh model 420 may be displayed on the 2D slices. For example, the intersection of the boundary 422 with respect to the 2D image slice 430 may be displayed on the 2D image slice 430 as intersections 438. The intersection of the 2D image slice 430 with the structure 426 may be displayed on the 2D image slice 430 as an intersection 442. Further, the intersections of the 2D image slice 430 with the first region 423 of the 3D mesh model 420 may be displayed on the 2D image slice 430 as intersection 444, while the intersections of the 2D image slice 430 with the second region 424 of the 3D mesh model 420 may be displayed on the 2D image slice 430 as intersections 439. The intersections displayed on the 2D image slice 430 may be colorized or otherwise styled to visually correspond to the regions and boundaries of the 3D mesh model 420, as depicted. Similarly, the intersections of the second 2D image slice 450 with the 3D mesh model 420 may be displayed on the 2D image slice 450 as intersections 458, 459, 462, 464, and 458. Further, the intersections of the third 2D image slice 470 with the 3D mesh model 420 may be displayed on the 2D image slice 470 as intersections 478, 479, 482, and 484. In this way, the user may easily identify the position of anatomical structures and regions of interest within the 2D image slices.

A technical effect of the disclosure is the generation of a three-dimensional model of a region of interest. Another technical effect of the disclosure is the display of intersection information on ultrasound images. Yet another technical effect of the disclosure is the updating of an ultrasound image responsive to user adjustments of intersections. Another technical effect of the disclosure is the simplified navigation of three-dimensional ultrasound data via a three-dimensional mesh model.

In one embodiment, a method comprises rendering a three-dimensional (3D) image and at least one two-dimensional (2D) image from a 3D dataset, generating a 3D model of at least a subset of the 3D dataset, identifying intersections between the 3D image, the at least one 2D image, and the 3D model, and displaying the 3D model and the intersections on the 3D model.

In a first example of the method, generating the 3D model comprises segmenting a region of interest (ROI) in the 3D image, generating a 3D mesh model for the ROI, and coupling the 3D mesh model to the segmented ROI in the 3D image. In a second example of the method optionally including the first example, the method further comprises displaying one or more of the 3D image and the at least one 2D image. In a third example of the method optionally including one or more of the first and second examples, the method further comprises displaying one or more visual indicators on the at least one 2D image corresponding to the intersections between the at least one 2D image and the 3D model. In a fourth example of the method optionally including one or more of the first through third examples, the method further comprises displaying the intersection of the at least one 2D image with the 3D model on the at least one 2D image. In a fifth example of the method optionally including one or more of the first through fourth examples, the method further comprises receiving a user-adjusted position of the intersection, generating a second 2D image based on the user-adjusted position of the intersection, and displaying the second 2D image in place of the at least one 2D image. In a sixth example of the method optionally including one or more of the first through fifth examples, the intersections comprise one or more of curves and planes visually overlaid on the 3D model. In a seventh example of the method optionally including one or more of the first through sixth examples, displaying the intersections comprises colorizing one or more voxels of the 3D model corresponding to the intersection between the at least one 2D image and the 3D model. In an eighth example of the method optionally including one or more of the first through seventh examples, the method further comprises acquiring the 3D dataset, wherein acquiring the 3D dataset comprises one of controlling an imaging device, such as an ultrasound probe, to acquire the 3D dataset, or accessing the 3D dataset in memory.

In another representation, a method comprises acquiring a three-dimensional (3D) ultrasound dataset, rendering a 3D image and a two-dimensional (2D) image from the 3D ultrasound dataset, generating a 3D model of at least a subset of the 3D ultrasound dataset, identifying intersections between the 3D image, the 2D image, and the 3D model, and displaying the 3D model, the 3D image, the 2D image, and the intersections at least on the 3D model.

In a first example of the method, generating the 3D model comprises segmenting a region of interest (ROI) in the 3D image, generating a 3D mesh model for the ROI, and coupling the 3D mesh model to the segmented ROI in the 3D image. In a second example of the method optionally including the first example, generating the 3D model comprises retrieving a 3D mesh model from a digital repository. In a third example of the method optionally including one or more of the first and second examples, the method further comprises displaying one or more visual indicators on the 2D image corresponding to the intersections between the 2D image and the 3D model. In a fourth example of the method optionally including one or more of the first through third examples, the intersections comprise one or more of curves and planes visually overlaid on the 3D model. In a fifth example of the method optionally including one or more of the first through fourth examples, displaying the intersections comprises colorizing one or more voxels of the 3D model corresponding to the intersection between the 2D image and the 3D model. In a sixth example of the method optionally including one or more of the first through fifth examples, the method further comprises displaying the intersection of the 2D image with the 3D model on the 2D image. In a seventh example of the method optionally including one or more of the first through sixth examples, the method further comprises receiving a user-adjusted position of the intersection, generating a second 2D image based on the user-adjusted position of the intersection, and displaying the second 2D image in place of the 2D image.

In another embodiment, a method comprises acquiring a three-dimensional (3D) ultrasound dataset of a region of interest (ROI), generating a 3D model of the ROI, generating a 3D image and a two-dimensional (2D) image slice from the 3D ultrasound dataset, displaying the 3D image, the 2D image slice, and the 3D model, displaying an intersection between the 3D image and the 2D image slice on the 3D model, receiving user input for an adjusted slice position with respect to the 3D model, generating a second 2D image slice from the 3D ultrasound dataset based on the adjusted slice position, and replacing the display of the 2D image slice with the second 2D image slice.

In a first example of the method, a position of the 2D image slice in the 3D ultrasound dataset is automatically determined based on the ROI. In a second example of the method optionally including the first example, a position of the 2D image slice in the 3D ultrasound dataset is manually input by a user. In a third example of the method optionally including one or more of the first and second examples, the method further comprises displaying an intersection between the 2D image slice and the 3D model on the 2D image slice. In a fourth example of the method optionally including one or more of the first through third examples, the method further comprises displaying the intersection between the 3D image and the 2D image slice on the 3D image. In a fifth example of the method optionally including one or more of the first through fourth examples, the intersection comprises a colorized curve.

In yet another embodiment, a system comprises a display device and a processor communicatively coupled to the display device, the processor configured with instructions in non-transitory memory that when executed cause the processor to: access a three-dimensional (3D) volumetric image dataset including a region of interest (ROI); render a 3D image and a two-dimensional (2D) image from the 3D volumetric image dataset; generate a 3D model of the ROI; identify intersections between the 3D image, the 2D image, and the 3D model; and output the 3D model and the intersections to the display device.

In a first example of the system, the system further comprises a user interface communicatively coupled to the processor, wherein the processor is further configured with instructions in the non-transitory memory that when executed cause the processor to adjust display on the display device of the 3D model responsive to user input received via the user interface. In a second example of the system optionally including the first example, the processor is further configured with instructions in the non-transitory memory that when executed cause the processor to receive, via the user interface, a user adjustment of a position of the intersection between the 2D image and the 3D model, generate a second 2D image based on the user adjustment, and output the second 2D image to the display device. In a third example of the system optionally including one or more of the first and second examples, adjusting the display of the 3D model comprises adjusting one or more of a scale and an orientation of the 3D model. In a fourth example of the system optionally including one or more of the first through third examples, generating the 3D model of the ROI comprises segmenting the ROI in the 3D image, generating a 3D mesh model for the ROI, and coupling the 3D mesh model to the segmented ROI in the 3D image. In a fifth example of the system optionally including one or more of the first through fourth examples, the processor is further configured with instructions in the non-transitory memory that when executed cause the processor to output, to the display device, one or more of the 3D image, the 2D image, and one or more visual indicators on the 2D image corresponding to the intersections between the 2D image and the 3D model. In a sixth example of the system optionally including one or more of the first through fifth examples, the system further comprises an ultrasound probe communicatively coupled to the processor and configured to acquire a 3D ultrasound dataset, wherein the 3D volumetric image dataset comprises the 3D ultrasound dataset.

In another representation, a system comprises an ultrasound probe configured to acquire a three-dimensional (3D) ultrasound dataset including a region of interest (ROI), a display device configured to display one or more ultrasound images generated from the 3D ultrasound dataset, and a processor communicatively coupled to the ultrasound probe and the display device, the processor configured with instructions in non-transitory memory that when executed cause the processor to: acquire, via the ultrasound probe, the 3D ultrasound dataset; render a 3D image and a two-dimensional (2D) image from the 3D ultrasound dataset; generate a 3D model of the ROI; identify intersections between the 3D image, the 2D image, and the 3D model; and output the 3D image, the 2D image, the 3D model, and the intersections to the display device.

In a first example of the system, the system further comprises a user interface communicatively coupled to the processor, wherein the processor is further configured with instructions in the non-transitory memory that when executed cause the processor to adjust display on the display device of the 3D model responsive to user input received via the user interface. In a second example of the system optionally including the first example, the processor is further configured with instructions in the non-transitory memory that when executed cause the processor to receive, via the user interface, a user adjustment of a position of the intersection between the 2D image and the 3D model, generate a second 2D image based on the user adjustment, and output the second 2D image to the display device. In a third example of the system optionally including one or more of the first and second examples, adjusting the display of the 3D model comprises adjusting one or more of a scale and an orientation of the 3D model. In a fourth example of the system optionally including one or more of the first through third examples, generating the 3D model of the ROI comprises segmenting the ROI in the 3D image, generating a 3D mesh model for the ROI, and coupling the 3D mesh model to the segmented ROI in the 3D image. In a fifth example of the system optionally including one or more of the first through fourth examples, the processor is further configured with instructions in the non-transitory memory that when executed cause the processor to output, to the display device, one or more visual indicators on the 2D image corresponding to the intersections between the 2D image and the 3D model.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
rendering a three-dimensional (3D) image and at least one two-dimensional (2D) image from a 3D dataset;
generating a 3D model of at least a subset of the 3D dataset;
identifying intersections between the 3D image, the at least one 2D image, and the 3D model, the intersections including intersections between the 3D image and the at least one 2D image, intersections between the 3D image and the 3D model, and intersections between the at least one 2D image and the 3D model;
displaying the 3D model with the intersections between the 3D image and the 3D model and the intersections between the at least one 2D image and the 3D model superimposed on the 3D model;
displaying the at least one 2D image with the intersections between the 3D image and the at least one 2D image and the intersections between the at least one 2D image and the 3D model superimposed on the at least one 2D image; and
displaying the 3D image with the intersections between the 3D image and the at least one 2D image and the intersections between the 3D image and the 3D model superimposed on the 3D image.

2. The method of claim 1, wherein generating the 3D model comprises segmenting a region of interest (ROI) in the 3D image, generating a 3D mesh model for the ROI, and coupling the 3D mesh model to the segmented ROI in the 3D image.

3. The method of claim 1, further comprising displaying the 3D image, the 3D model, and the at least one 2D image adjacent to each other via a display device, wherein the 3D image comprises a 3D image of at least a portion of a heart.

4. The method of claim 3, further comprising displaying one or more visual indicators on the at least one 2D image corresponding to the intersections between the at least one 2D image and the 3D model.

5. The method of claim 2, wherein the intersections between the 3D image, the at least one 2D image, and the 3D model are identified based on the coupling of the 3D mesh model to the segmented ROI in the 3D image.

6. The method of claim 3, further comprising receiving a user-adjusted position of an intersection, generating a second 2D image based on the user-adjusted position of the intersection, and displaying the second 2D image in place of the at least one 2D image.

7. The method of claim 1, wherein the intersections between the at least one 2D image and the 3D model comprise an intersection between the at least one 2D image and a structure of the 3D model, the structure corresponding to a mitral valve.

8. The method of claim 1, wherein displaying the intersections comprises colorizing one or more voxels of the 3D model corresponding to the intersection between the at least one 2D image and the 3D model, and wherein the intersections comprise one or more of curves and planes visually overlaid on the 3D model.

9. The method of claim 1, further comprising acquiring the 3D dataset, wherein acquiring the 3D dataset comprises one of controlling an ultrasound imaging device to acquire the 3D dataset or accessing the 3D dataset in memory, the 3D dataset comprising echocardiography data.

10. A method, comprising:
acquiring a three-dimensional (3D) ultrasound dataset of a region of interest (ROI);
generating a 3D model of the ROI;
generating a 3D image and a two-dimensional (2D) image slice from the 3D ultrasound dataset;
coupling the 3D model to the 3D image;
displaying the 3D image, the 2D image slice, and the 3D model separately on a display device;
displaying an intersection between the 3D image and the 2D image slice on the 3D model, wherein a position of the intersection displayed on the 3D model is based on the coupling of the 3D model to the 3D image;
receiving user input for an adjusted slice position with respect to the 3D model;
generating a second 2D image slice from the 3D ultrasound dataset based on the adjusted slice position and the coupling of the 3D model to the 3D image; and
replacing the display of the 2D image slice with the second 2D image slice.

11. The method of claim 10, wherein a position of the 2D image slice in the 3D ultrasound dataset is automatically determined based on the ROI or manually input by a user.

12. The method of claim 10, further comprising displaying an intersection between the 2D image slice and the 3D model on the 2D image slice, wherein the ROI comprises a heart and the 3D model includes a structure corresponding to a mitral valve of the heart, wherein the intersection between the 2D image slice and the 3D model comprises an intersection between the 2D image slice and the structure of the 3D model.

13. The method of claim 10, further comprising displaying the intersection between the 3D image and the 2D image slice on the 3D image.

14. A system, comprising:
a display device; and
a processor communicatively coupled to the display device, the processor configured with instructions in non-transitory memory that, when executed, cause the processor to:
access a three-dimensional (3D) volumetric image dataset including a region of interest (ROI);
render a 3D image and a two-dimensional (2D) image from the 3D volumetric image dataset;
generate a 3D model of the ROI;
identify intersections between the 3D image, the 2D image, and the 3D model, the intersections including intersections between the 3D image and the 2D image, intersections between the 3D image and the 3D model, and intersections between the 2D image and the 3D model;
display, via the display device, the 3D model with the intersections between the 3D image and the 3D model and the intersections between the 2D image and the 3D model superimposed on the 3D model;
display, via the display device, the 2D image with the intersections between the 3D image and the 2D image and the intersections between the 2D image and the 3D model superimposed on the 2D image; and
display, via the display device, the 3D image with the intersections between the 3D image and the 2D image and the intersections between the 3D image and the 3D model superimposed on the 3D image.

15. The system of claim 14, further comprising a user interface communicatively coupled to the processor, wherein the processor is further configured with instructions in the non-transitory memory that, when executed, cause the processor to adjust the display on the display device of the 3D model responsive to user input received via the user interface.

16. The system of claim 15, wherein the processor is further configured with instructions in the non-transitory memory that, when executed, cause the processor to receive, via the user interface, a user adjustment of a position of the intersection between the 2D image and the 3D model, generate a second 2D image based on the user adjustment, and output the second 2D image to the display device.

17. The system of claim 15, wherein adjusting the display of the 3D model comprises adjusting one or more of a scale and an orientation of the 3D model, and updating, based on adjustments to one or more of the scale and the orientation of the 3D model, the display of the intersections between the 3D image and the 3D model and the intersections between the 2D image and the 3D model superimposed on the 3D model.

18. The system of claim 14, wherein generating the 3D model of the ROI comprises segmenting the ROI in the 3D image, generating a 3D mesh model for the ROI, and coupling the 3D mesh model to the segmented ROI in the 3D image.

19. The system of claim 18, wherein the processor is further configured with instructions in the non-transitory memory that, when executed, cause the processor to position the intersections between the 2D image and the 3D model superimposed on the 3D model based on the coupling of the 3D mesh model to the segmented ROI in the 3D image.

20. The system of claim 14, further comprising an ultrasound probe communicatively coupled to the processor and configured to acquire a 3D cardiac ultrasound dataset, wherein the 3D volumetric image dataset comprises the 3D cardiac ultrasound dataset, wherein the ROI comprises a heart, and wherein the 3D model includes a structure corresponding to a mitral valve of the heart.

* * * * *